(12) United States Patent
Alcaraz et al.

(10) Patent No.: US 9,868,740 B2
(45) Date of Patent: *Jan. 16, 2018

(54) PYRIMIDINONE COMPOUNDS WHICH ARE HNE INHIBITORS

(71) Applicant: CHIESI FARMACEUTICI S.p.A., Parma (IT)

(72) Inventors: Lilian Alcaraz, Harlow (GB); Robert Andrew Heald, Harlow (GB); Jonathan Mark Sutton, Harlow (GB); Elisabetta Armani, Parma (IT); Carmelida Capaldi, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/317,274

(22) PCT Filed: Jun. 12, 2014

(86) PCT No.: PCT/EP2014/062254
§ 371 (c)(1),
(2) Date: Dec. 8, 2016

(87) PCT Pub. No.: WO2015/188866
PCT Pub. Date: Dec. 17, 2015

(65) Prior Publication Data
US 2017/0101413 A1   Apr. 13, 2017

(51) Int. Cl.
*C07D 487/04* (2006.01)
*A61K 31/519* (2006.01)
*A61P 11/06* (2006.01)
*A61P 11/08* (2006.01)
*A61P 11/12* (2006.01)
*A61P 11/00* (2006.01)

(52) U.S. Cl.
CPC .................. *C07D 487/04* (2013.01)

(58) Field of Classification Search
CPC ..................... C07D 487/04; A61K 31/519
See application file for complete search history.

(56) References Cited

U.S. PATENT DOCUMENTS

| | | |
|---|---|---|
| 2013/0065913 A1 | 3/2013 | Blench et al. |
| 2013/0123278 A1 | 5/2013 | Edwards et al. |
| 2013/0150380 A1 | 6/2013 | Edwards et al. |
| 2014/0171414 A1 | 6/2014 | Alcaraz et al. |
| 2014/0179714 A1 | 6/2014 | Blench et al. |

FOREIGN PATENT DOCUMENTS

| | | |
|---|---|---|
| WO | 2011/110858 A1 | 9/2011 |
| WO | 2011/110859 A1 | 9/2011 |
| WO | 2013/037809 A1 | 3/2013 |
| WO | 2014/095700 A1 | 6/2014 |

OTHER PUBLICATIONS von Nussbaum et al. Bioorganic & Medicinal Chemistry Letters 2015, 25, 4370-4381.*
International Search Report dated Jul. 25, 2014 in PCT/EP2014/062254 filed Jun. 12, 2014.

* cited by examiner

*Primary Examiner* — Susanna Moore
(74) *Attorney, Agent, or Firm* — Oblon, McClelland, Maier & Neustadt, L.L.P.

(57) ABSTRACT

This invention relates to heterocyclic compounds, which are pyrimidinone derivatives having human neutrophil elastase inhibitory properties, and their use in therapy.

13 Claims, No Drawings

PYRIMIDINONE COMPOUNDS WHICH ARE HNE INHIBITORS

FIELD OF THE INVENTION

This invention relates to heterocyclic compounds, which are pyrimidinone derivatives having human neutrophil elastase inhibitory properties, and their use in therapy.

BACKGROUND TO THE INVENTION

Human neutrophil elastase (HNE) is a 32 kDa serine proteinase found in the azurophilic granules of neutrophils. It has a role in the degradation of a wide range of extracellular matrix proteins, including fibronectin, laminin, proteoglycans, Type III and Type IV collagens as well as elastin (Bieth, G. in *Regulation of Matrix accumulation*, Mecham, R. P. (Eds), Academic Press, NY, USA 1986, 217-306). HNE has long been considered to play an important role in homeostasis through repair and disposal of damaged tissues via degradation of the tissue structural proteins. It is also relevant in the defense against bacterial invasion by means of degradation of the bacterial body. In addition to its effects on matrix tissues, HNE has been implicated in the upregulation of IL-8 gene expression and also induces IL-8 release from the epithelial cells of the lung. In animal models of Chronic Obstructive Pulmonary Disease induced by tobacco smoke exposure both small molecule inhibitors and protein inhibitors of HNE inhibit the inflammatory response and the development of emphysema (Wright, J. L. et al. *Am. J. Respir. Crit. Care Med.* 2002, 166, 954-960; Churg, A. et al. *Am. J. Respir. Crit. Care Med.* 2003, 168, 199-207). Thus, HNE may play a role both in matrix destruction and in amplifying inflammatory responses in chronic respiratory diseases where neutrophil influx is a characteristic feature. Indeed, FINE is believed to play a role in several pulmonary diseases, including chronic obstructive pulmonary disease (COPD), cystic fibrosis (CF), acute respiratory distress syndrome (ARDS), pulmonary emphysema, pneumonia and lung fibrosis. It is also implicated in several cardiovascular diseases in which tissue remodelling is involved, for example, in heart failure and the generation of ischaemic tissue injury following acute myocardial infarction.

COPD is an umbrella term encompassing three different pathological conditions, all of which contribute to limitation of airflow: chronic bronchitis, emphysema and small-airway disease. Generally all three will exist to varying extents in patients presenting with COPD, and all three may be due to neutrophil-mediated inflammation, as supported by the increased number of neutrophils observed in bronchoalveolar leakage (BAL) fluids of COPD patients (Thompson, A. B.; Daughton, D.; et al. *Am. Rev. Respir. Dis.* 1989, 140, 1527-1537). The major pathogenic determinant in COPD has long been considered to be the protease-anti-protease balance (also known as the "elastase:anti-elastase hypothesis"), in which an imbalance of FINE and endogenous antiproteases such as α1-antitrypsin ($\alpha_1$-AT), secretory leukocyte protease inhibitor (SLPI) and pre-elafin leads to the various inflammatory disorders of COPD. Individuals that have a genetic deficiency of the protease inhibitor al-antitrypsin develop emphysema that increases in severity over time (Laurrell, C. B.; Erikkson, S Scand. *J. Clin. Invest.* 1963 15, 132-140). An excess of HNE is therefore destructive, leading to the breakdown of pulmonary morphology with loss of elasticity and destruction of alveolar attachments of airways in the lung (emphysema) whilst simultaneously increasing microvascular permeability and mucus hypersecretion (chronic bronchitis).

Several human neutrophil inhibitors have need disclosed so far in the art. In particular, International Patent Applications n. WO2011/110858 and n. WO2011/110859 describe some pyrimidine derivatives having human neutrophil elastase inhibitory properties and their use in therapy.

Although several HNE inhibitors have been disclosed so far as above reported, there is still a need for further FINE inhibitors. Particularly, there is still a need for further FINE inhibitors endowed with a high potency for FINE enzyme inhibition. Particularly advantageous would also be the identification of further FINE inhibitors endowed with a high potency for FINE enzyme inhibition and which would show an appropriate developability profile as an inhalation treatment.

The present invention addresses the above mentioned need by providing the compounds of the invention.

Other FINE inhibitors are described in the co-pending application PCT/EP2013/076672.

BRIEF DESCRIPTION OF THE INVENTION

This invention provides novel compounds which are inhibitors of FINE, and are useful in the treatment of diseases or conditions in which FINE activity plays a part.

SUMMARY OF THE INVENTION

The present invention relates to compounds which are FINE inhibitors falling within the scope of Formula (I) of No. PCT/EP2013/076672, but not specifically disclosed therein.

DETAILED DESCRIPTION OF THE INVENTION

According to the present invention, there is provided a compound selected from the group consisting of:

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-4-methoxy-pyridinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-hydroxy-pyridinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2-methyl-pyridinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-4-hydroxymethyl-pyridinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-4-isopropyl-pyridinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-5-hydroxy-2-methyl-pyridinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2,4-dimethyl-pyridinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3,5-dimethyl-pyridinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2-ethyl-pyridinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2-(2-hydroxy-ethyl)-pyridinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-4-ethyl-pyridinium bromide.

In particular, the present invention provides a compound selected from the group consisting of those of listed in the Table herebelow, or a pharmaceutically acceptable salt thereof:

| Compound Name | Ex. N. |
|---|---|
| 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-4-methoxy-pyridinium bromide | 1 |
| 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-hydroxy-pyridinium bromide | 2 |
| 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2-methyl-pyridinium bromide | 3 |
| 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-4-hydroxymethyl-pyridinium bromide | 4 |
| 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-4-isopropyl-pyridinium bromide | 5 |
| 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-5-hydroxy-2-methyl-pyridinium bromide | 6 |
| 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2,4-dimethyl-pyridinium bromide | 7 |
| 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3,5-dimemyl-pyridinium bromide | 8 |
| 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2-ethyl-pyridinium bromide | 9 |
| 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2-(2-hydroxy-ethyl)-pyridinium bromide | 10 |
| 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-4-ethyl-pyridinium bromide | 11 |

The compounds of the invention may be prepared in the form of salts, particularly pharmaceutically acceptable salts, N-oxides, hydrates, solvates and polymorphs thereof. Any reference to a compound herein, or reference to "compounds of the invention", and the like includes such compounds whether or not in salt, N-oxide, hydrate, solvate or polymorphic form.

Compounds of the invention may be used in the treatment or prevention of diseases in which HNE is implicated, for example chronic obstructive pulmonary disease (COPD), bronchiectasis, chronic bronchitis, lung fibrosis, pneumonia, acute respiratory distress syndrome (ARDS), pulmonary emphysema, smoking-induced emphysema and cystic fibrosis.

Hence other aspects of the invention are (i) a pharmaceutical composition comprising a compound of the invention and a pharmaceutically acceptable carrier or excipient; and (ii) the use of a compound of the invention for the manufacture of a medicament for the treatment or prevention of a disease or condition in which HNE is implicated.

The term "salt" includes base addition and acid addition salts.

The term "Pharmaceutically acceptable salts" refers to derivatives of compounds of the invention wherein the parent compound is suitably modified by converting any of the free acid or basic group, if present, into the corresponding addition salt with any base or acid conventionally intended as being pharmaceutically acceptable.

Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)amino-methane, L-arginine, L-lysine, N-ethyl piperidine, dibenzylamine and the like. Those compounds which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like. Those compounds which have quaternary nitrogen can also form quaternary salts with a pharmaceutically acceptable counter-ion such as chloride, bromide, acetate, formate, p-toluenesulfonate, succinate, hemi-succinate, naphthalene-bis sulfonate, methanesulfonate, xinafoate, and the like.

Where the compounds of the invention have at least one stereogenic center, they may exist as enantiomers. When the compounds according to the invention possess two or more stereogenic centers, they may additionally exist as diastereoisomers. It is to be understood that all such isomers and mixtures thereof in any proportion are encompassed within the scope of the present invention.

It will be apparent that the compounds of the invention represented by general formula (I), at least contain one stereogenic center, namely represented by the carbon atom (1), and therefore exist as optical stereoisomers

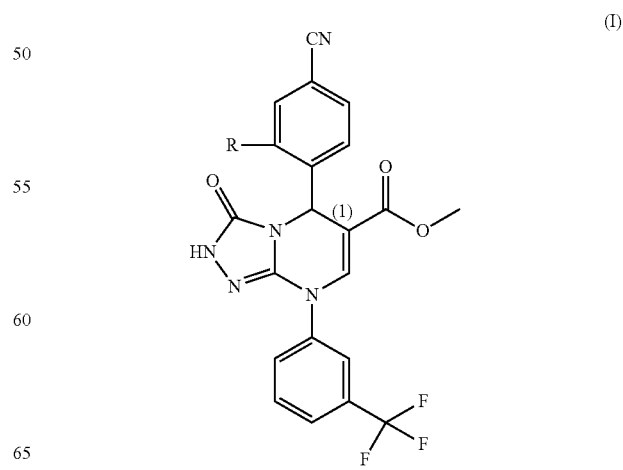

(I)

In one embodiment, the present invention is directed to compounds of formula (I)', which are compounds of formula (I) as above defined where the absolute configuration of carbon (1) is that shown here below

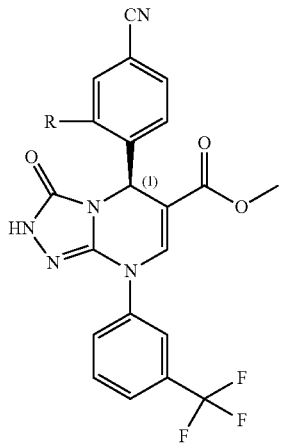

(I)'

In another embodiment, the present invention is directed to compounds of formula (I)'', which are compounds of formula (I) as above defined where the absolute configuration of carbon (1) is that shown herebelow:

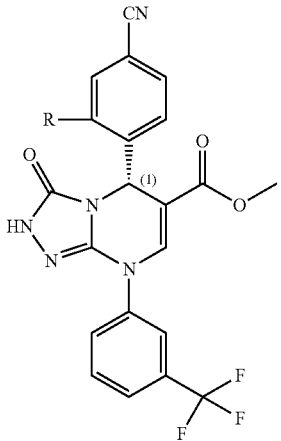

(I)''

The absolute configuration for carbon (1) is assigned on the basis of Cahn-Ingold-Prelog nomenclature based on groups' priorities.

EMBODIMENTS OF THE INVENTION

The compounds of invention are compounds of formula (I) and more specifically, compounds of formula (I)'' or pharmaceutically acceptable salts thereof wherein the group R is selected in the group consisting of
4-methoxy-pyridinyl;
3-hydroxy-pyridinyl;
2-methyl-pyridinyl;
4-hydroxymethyl-pyridinyl;
4-isopropyl-pyridinyl;
5-hydroxy-2-methyl-pyridinyl;
2,4-dimethyl-pyridinyl;
3,5-dimethyl-pyridinyl;
2-ethyl-pyridinyl;
2-(2-hydroxy-ethyl)-pyridinyl; and
4-ethyl-pyridinyl.

Utility

The therapeutic utility of the present compounds is pertinent to any disease that is known to be at least partially mediated by the action of human neutrophil elastase. For example, the present compounds may be beneficial in the treatment of chronic obstructive pulmonary disease (COPD), cystic fibrosis (CF), bronchiectasis, acute respiratory distress syndrome (ARDS), pulmonary emphysema, pneumonia and lung fibrosis.

Compounds of the invention are useful for treatment of inflammatory respiratory disorders, for example asthma (mild, moderate or severe), steroid resistant asthma, bronchitis, chronic obstructive pulmonary disease (COPD), cystic fibrosis (CF), pulmonary edema, pulmonary embolism, pneumonia, pulmonary sarcoidosis, pulmonary emphysema, silicosis, pulmonary fibrosis, pulmonary hypertension, respiratory failure, acute respiratory distress syndrome (ARDS), emphysema, chronic bronchitis, tuberculosis, aspergillosis and other fungal infections, hypersensitivity pneumonitis, vasculitic and thrombotic disorders of the lung vasculature, antitussive activity including treatment of chronic cough associated with inflammatory and secretory conditions of the airways, infection due to respiratory syncytial virus, influenza, coronavirus (including severe acute respiratory syndrome, SARS) and adenovirus, bronchiectasis and lung cancer.

The present invention is also concerned with pharmaceutical formulations comprising, as an active ingredient, a compound of the invention. Other compounds may be combined with compounds of this invention for the prevention and treatment of inflammatory diseases of the lung.

Thus the present invention is also concerned with pharmaceutical compositions for preventing and treating inflammatory diseases of the lung comprising a therapeutically effective amount of a compound of the invention and one or more other therapeutic agents.

Combinations

Suitable therapeutic agents for a combination therapy with compounds of the invention include: (1) a corticosteroid, for example budesonide, beclomethasone, beclomethasone (e.g., as the mono or the dipropionate ester), flunisolide, fluticasone (e.g. as the propionate or furoate ester), Ciclesonide, mometasone (e.g. as the furoate ester), mometasone desonide, rofleponide, hydrocortisone, prednisone, prednisolone, methyl prednisolone, naflocort, deflazacort, halopredone acetate, fluocinolone acetonide, fluocinonide, clocortolone, tipredane, prednicarbate, alclometasone dipropionate, halometasone, rimexolone, deprodone propionate, triamcinolone, betamethasone, fludrocortisone, desoxycorticosterone, rofleponide, etiprednol dicloacetate and the like. Steroid drugs can additionally include steroids in clinical or pre-clinical development for respiratory diseases such as GW-685698, GW-799943, GSK 870086, QAE397, NCX-1010, NCX-1020, NO-dexamethasone, PL-2146, NS-126 (formerly ST-126). Steroid drugs can also additionally include next generation molecules in development with reduced side effect profiles such as selective glucocorticoid receptor agonists (SEGRAs), including ZK-216348 and AZD5423; (2) a β2-adrenoreceptor agonist, such as albuterol, bambuterol, terbutaline, fenoterol, formoterol, formoterol fumarate, salmeterol, salmeterol xinafoate, arformoterol, arfomoterol tartrate, indacaterol (QAB-149), carmoterol, BI 1744 CL, GSK159797 (milveterol), GSK59790, GSK159802, GSK642444 (vilanterol), GSK678007, GSK96108, clenbuterol, procaterol, bitolterol, LAS100977 (abediterol), BI1744CL (olodaterol) and brodxaterol; (3) a leukotriene modulator, for example montelukast, zafirlukast or pranlukast; (4) anticholinergic agents, for example selective muscarinic-3 (M3) receptor antagonists such as ipratropium bromide, tiotropium, tiotropium bromide (Spiriva®), glycopyrronium bromide, aclidinium bromide, LAS34273, GSK656398, GSK233705, GSK 573719 (umeclidinium), LAS35201, QAT370 and oxytropium bromide; (5) phosphodiesterase-IV (PDE-IV) inhibitors, for example roflumilast, cilomilast or theophylline; (6) an antitussive agent, such as codeine or dextramorphan; and (7) a non-steroidal anti-inflammatory agent (NSAID), for example ibuprofen or ketoprofen; (8) a mucolytic, for example N acetyl cysteine or fudostein; (9) an expectorant/mucokinetic modulator, for example ambroxol, hypertonic solutions (e.g. saline or mannitol) or surfactant; (10) a peptide mucolytic, for example recombinant human deoxyribonuclease I (dornase-alfa and rhDNase) or helicidin; (11) antibiotics, for example azithromycin, tobramycin and aztreonam; and (12) p38 Mitogen Activated Protein (MAP) kinase inhibitors, such as GSK 856553 and GSK 681323; (12) inhibitors of Janus Kinases (JAK) such as CP-690550 or GLPG0634; (13) Spleen Tyrosine Kinase (SYK) inhibitors such as R406, R343 or PRT062607; (14) inhibitors of delta and/or gamma isoforms of Phosphatidylinositol 3-kinase (PI3K).; (15) anti-retroviral agents such as ribavirin, zanamivir or laninamivir; (16) PPAR-γ agonists such as pioglitazone and rosiglitazone.

In one aspect, the invention provides for the use of inhaled administration of compounds of the invention in combination with other anti-inflammatory drugs and bronchodilator drug combinations (i.e. triple combination product), including but not limited to salmeterol xinafoate/fluticasone propionate (Advair/Seretide®), vilanterol/fluticasone furoate (BREO ELLIPTA™), formoterol fumarate/budesonide (Symbicort®), formoterol fumarate/mometasone furoate, formoterol fumarate/beclometasone dipropionate (Foster®), formoterol fumarate/fluticasone propionate (FlutiForm®), Indacaterol/mometasone furoate, Indacaterol/QAE-397, GSK159797/GSK 685698, GSK159802/GSK 685698, GSK642444/GSK 685698, formoterol fumarate/ciclesonide, arformoterol tartrate/ciclesonide.

In another aspect, the invention provides for the use of inhaled administration of compounds of the invention in combination with other bronchodilator drug combinations, particularly $\beta_2$ agonist/$M_3$ antagonist combinations (i.e. triple combination product), including but not limited to salmeterol xinafoate/tiotropium bromide, formoterol fumarate/tiotropium bromide, formoterol fumarate/glycopyrrolate (PT003), BI 1744 CL/tiotropium bromide, indacaterol/NVA237, indacaterol/QAT-370, formoterol/LAS34273, umeclidinium/vilanterol (Anoro™), GSK159797/GSK 573719, GSK159802/GSK 573719, GSK642444/GSK 573719, GSK159797/GSK 233705, GSK159802/GSK 233705, GSK642444/GSK 233705.

The weight ratio of the first and second active ingredients may be varied and will depend upon the effective dose of each ingredient. Generally, an effective dose of each will be used.

The magnitude of prophylactic or therapeutic dose of a compound of the invention will, of course, vary with the nature of the severity of the condition to be treated and with the particular compound and its route of administration, and will generally be determined by clinical trial as required in the pharmaceutical art. It will also vary according to the age, weight and response of the individual patient. In general, the daily dose range will lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

Compositions

Another aspect of the present invention provides pharmaceutical compositions which comprise a compound of the invention and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the invention encompass any composition made by admixing a compound of the invention, additional active ingredient(s), and pharmaceutically acceptable excipients.-

The pharmaceutical compositions of the invention comprise a compound of the invention as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Any suitable route of administration may be employed for providing a mammal, especially a human, with an effective dosage of a compound of the present invention. In therapeutic use, the active compound may be administered by any convenient, suitable or effective route. Suitable routes of administration are known, and include oral, intravenous, rectal, parenteral, topical, ocular, nasal, buccal and pulmonary (by inhalation).

Compositions suitable for administration by inhalation are known, and may include carriers and/or diluents that are known for use in such compositions. The composition may contain 0.01-99% by weight of active compound. Preferably, a unit dose comprises the active compound in an amount of 1 µg to 10 mg.

The most suitable dosage level may be determined by any known suitable method. It will be understood, however, that the specific amount for any particular patient will depend upon a variety of factors, including the activity of the specific compound that is used, the age, body weight, diet, general health and sex of the patient, time of administration, the route of administration, the rate of excretion, the use of any other drugs, and the severity of the disease to be treated.

For delivery by inhalation, the active compound is preferably in the form of microparticles. They may be prepared by a variety of techniques, including spray-drying, freeze-drying and micronisation.

By way of example, a composition of the invention may be prepared as a suspension for delivery from a nebuliser or as an aerosol in a liquid propellant, for example for use in a pressurised metered dose inhaler (PMDI). Propellants suitable for use in a PMDI are known to the skilled person, and include CFC-12, HFA-134a, HFA-227, HCFC-22 (CC12F2) and HFA-152 (CH4F2 and isobutane).

In a preferred embodiment of the invention, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 µm.

In the case of an aerosol-based formulation, a preferred composition is:

| | |
|---|---|
| Compound of the invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

Compounds of the invention may be used in combination with other drugs that are used in the treatment/prevention/suppression or amelioration of the diseases or conditions for which present compounds are useful. Such other drugs may be administered, by a route and in an amount commonly used therefore, contemporaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients, in addition to a compound of the invention.

The agents of the invention may be administered in inhaled form. Aerosol generation can be carried out using, for example, pressure-driven jet atomizers or ultrasonic atomizers, preferably using propellant-driven metered aerosols or propellant-free administration of micronised active compounds from, for example, inhalation capsules or other "dry powder" delivery systems.

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321).

Methods of Synthesis

In one aspect of the invention, a process for the preparation of compounds of formula (I) is provided, according to general synthetic routes reported in Scheme A here below.

Scheme A

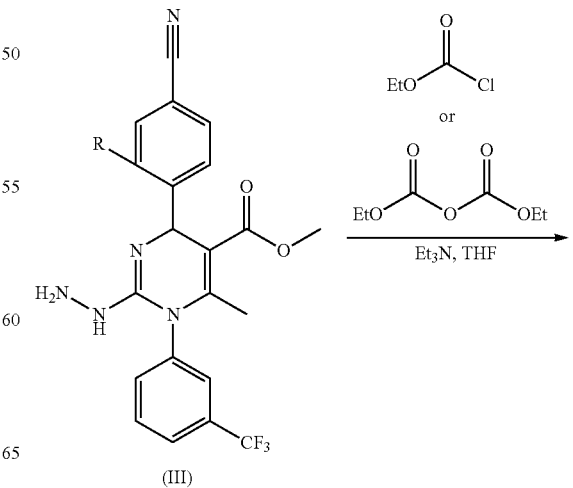

(III)

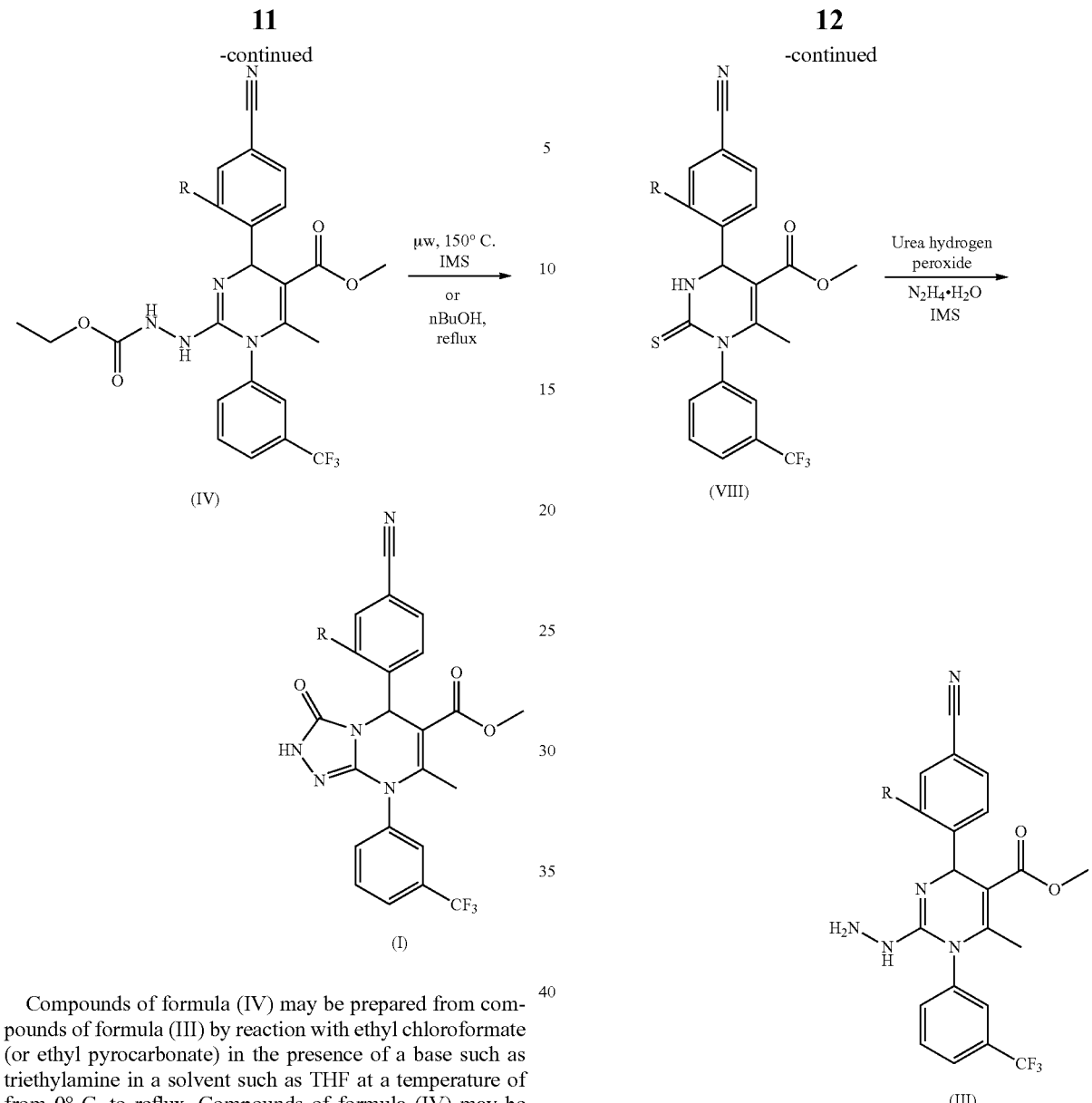

Compounds of formula (IV) may be prepared from compounds of formula (III) by reaction with ethyl chloroformate (or ethyl pyrocarbonate) in the presence of a base such as triethylamine in a solvent such as THF at a temperature of from 0° C. to reflux. Compounds of formula (IV) may be transformed into compounds of formula (I) by heating in an appropriate solvent. Suitable conditions include the use of a solvent such as IMS and heating using microwave irradiation at a temperature of up to 150° C. or conventional heating in a solvent such as n-butanol at reflux.

Compounds of formula (III) may be prepared according to Scheme B below:

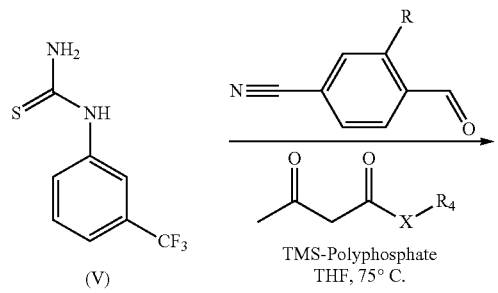

Compounds of formula (V) may be reacted with a benzaldehyde such as 3-bromo-4-formyl-benzonitrile and an acetoacetate such as ethyl acetoacetate in the presence of an acid such as TMS-polyphosphate in a solvent such as THF at a temperature of from room temperature to reflux to give compounds of formula (VIII)). Compounds of formula (III) may be prepared from compounds of formula (VIII) by reaction with an oxidizing agent such as urea hydrogen peroxide followed by in-situ treatment with hydrazine hydrate in IMS.

Furthermore compounds of formula (I)″, which are compounds of formula (I) as above defined where the absolute configuration of carbon (1) is that shown herebelow can be prepared according to Scheme C.

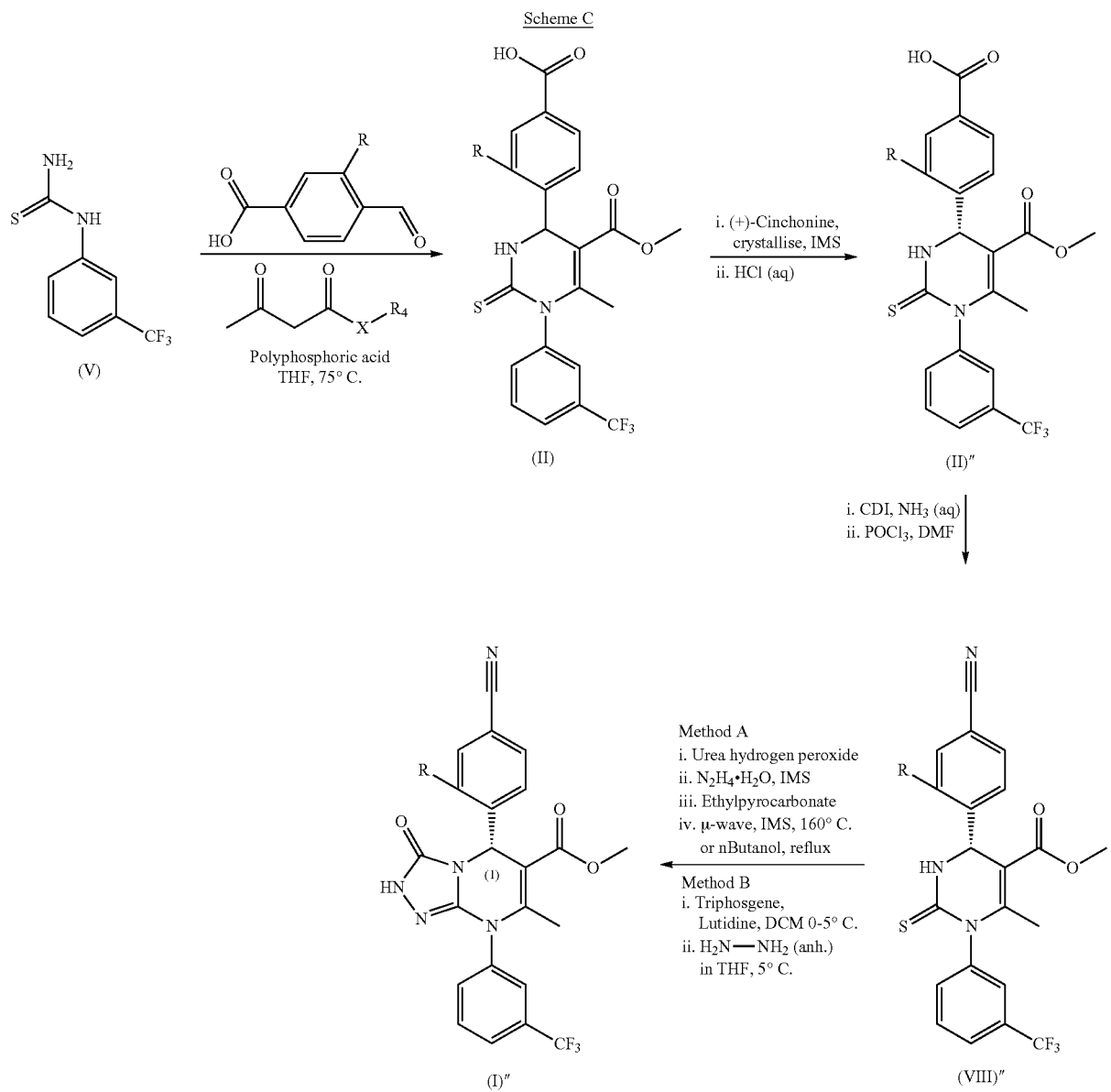

Scheme C

Compounds of formula (II) may be obtained from compounds of formula (V) by reacting with 3-bromo-4-formylbenzoic acid using a similar method described for the transformation of compounds of formula (V) to compounds of formula (VIII) in Scheme B. Compounds of formula (II)″, which are compounds of formula (II) wherein the absolute configuration at stereogenic center (1) is as reported in Scheme C, may be obtained from compounds of formula (II) by forming a chiral diastereomeric salt with a suitable chiral amine such as (+)-Cinchonine in a suitable solvent such as dioxane, followed by treatment of the salt with an acid such as hydrochloric acid to give the enantiomerically pure compounds of formula (II)″. Compounds of formula (VIII)″, which are compounds of formula (VIII) wherein the absolute configuration at stereogenic center (1) is as reported in Scheme C, may be prepared from compounds of formula (II)″ by reaction with aqueous ammonia in the presence of a coupling agent such as carbonyl diimidazole in a solvent such as THF at a temperature of from 0° C. to room temperature to give the intermediate primary amide. Conversion of the amide to compounds of formula (VIII)″ may be carried out using a dehydrating agent. Suitable conditions include the use of a solvent such as DMF and a dehydrating agent such as phosphorus oxychloride at a temperature of from 0° C. to room temperature.

Compounds of formula (I)″, which are compounds of formula (I) as above defined and wherein the absolute configuration of carbon (1) is that shown in Scheme C (Method A), may be obtained from compounds of formula (VIII)″ using similar methods described for the transformation of compounds of formula (VIII) to compounds of formula of formula (I) in Scheme A. Alternatively, compounds of formula (I)″, which are compounds of formula (I) as above defined and wherein the absolute configuration of carbon (1) is that shown in Scheme C may be also be obtained from compounds of formula (VIII)" using method B; wherein compounds of formula (VIII)" may be reacted with a chlorocarbonyl-containing/releasing compound such as phosgene or triphosgene and anhydrous hydrazine in the presence of a base such as 2,6-lutadine in a solvent such as dichloromethane at a temperature of from −5-5° C. to give compounds of formula (I)" wherein all other groups are as define for compounds of formula (I).

The skilled person would understand that by selecting of the appropriate chiral amine and its absolute configuration, derivatives of formula (II)', (VIII)', and (Ia)' [which are compounds of formula (II), (VIII) and (I), respectively wherein the absolute configuration at stereogenic center (1) is opposite to that reported in Scheme C] may be obtained.

The skilled person may introduce, where appropriate, suitable variations to the conditions specifically described in the experimentals in order to adapt the synthetic routes to the provision of further compounds of the invention. Such variations may include, but are not limited to, use of appropriate starting materials to generate different compounds, changes in the solvent and temperature of reactions, replacement of reactives with analogous chemical role, introduction or removal of protection/de-protection stages of functional groups sensitive to reaction conditions and reagents, as well as introduction or removal of specific synthetic steps oriented to further functionalisation of the chemical scaffold.

Processes which can be used and are described and reported in Examples should not be viewed as limiting the scope of the synthetic methods available for the preparation of the compounds of the invention.

Compounds used as starting materials or intermediates may be commercially available, their preparation may be specifically described in the literature or they may be prepared according to methods available in the literature and well known to the person skilled in the art.

The process described is particularly advantageous as it is susceptible of being properly modulated, through any proper variant known to the skilled person, so as to obtain any of the desired compounds of the invention. Such variants are comprised within the scope of the present invention.

From all of the above, it should be clear to the skilled person that any of the described groups may be present as such or in any properly protected form. In particular, functional groups present in the Intermediates and Examples and which could generate unwanted side reaction and by-products, need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known to those skilled in the art [see, for a general reference, T. W. Green; Protective Groups in Organic Synthesis (Wiley, N.Y. 1981)].

Likewise, selective protection and de-protection of any of the said groups, for instance including carbonyl, hydroxyl or amino groups, may be accomplished according to very well known methods commonly employed in organic synthetic chemistry.

Optional salt formation of the compounds of formula (I) may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

The diastereoisomers of compounds of formula (I), where available, may be obtained according to methods well known in the art, such as for example by preparative HPLC or by chromatographic purifications. A racemic mixture of compounds of formula (I) may as well be separated using preparative HPLC and a column with a chiral stationary phase, or resolved to yield individual enantiomers using methods well known in the art. Furthermore, chiral intermediates may be resolved and used to prepare chiral compounds of the invention.

From all of the above, it should be clear to the skilled person that the above process, comprehensive of any variant thereof for the preparation of suitable compounds of the invention, may be conveniently modified so as to adapt the reaction conditions to the specific needs, for instance by choosing appropriate condensing agents, solvents and protective groups, as the case may be.

Compounds of formula (Ia), i.e. compounds of formula (I) wherein R is a group as defined above, may be prepared according to Scheme D. Compounds of formula (IX), which are compounds of formula (I) wherein R is bromine or other suitable activating group taken from the group, but not exclusively, Cl, I, OTf, may be prepared according to Schemes A and B. It must appreciated that chiral compounds of the formula (I)" may also be prepared similarly according to Scheme C.

A compound of formula (XI) may be prepared from a compound of formula (IX). A compound of formula (XI) may be prepared using Heck coupling chemistry by reaction with an appropriately substituted vinyl compound (X) in the presence of an appropriate catalyst/ligand system such as Herrmann-Beller catalyst/tributylphosphine tetrafluoroborate in a solvent such as tetraethylene glycol or dimethoxyethane in the presence of a base such as pentamethylpiperidine at a temperature of from room temperature to 160° C. A compound of formula (XII) may be prepared from compounds of formula (XI) following hydrolysis and reduction steps using an acid such as trifluoroacetic acid in a solvent such as DCM at −10° C. to give the intermediate aldehyde, and a reducing agent such as sodium borohydride in a solvent such as MeOH at a temperature of from 0° C. to room temperature to give a compound of formula (XII). A compound of formula (XIII) can be prepared from a compound of formula (XII) using a mixture of carbon tetrabromide/triphenyl phosphine in a solvent such as DCM at a temperature of from 0° C. to 50° C. Typically, compounds of formula (I) may be obtained from compounds of formula (XIII) by reaction with a substituted pyridine, $R_1R_2$-Pyr (XIX) in a solvent such as acetonitrile at a temperature of from room temperature to 80° C.

Scheme D

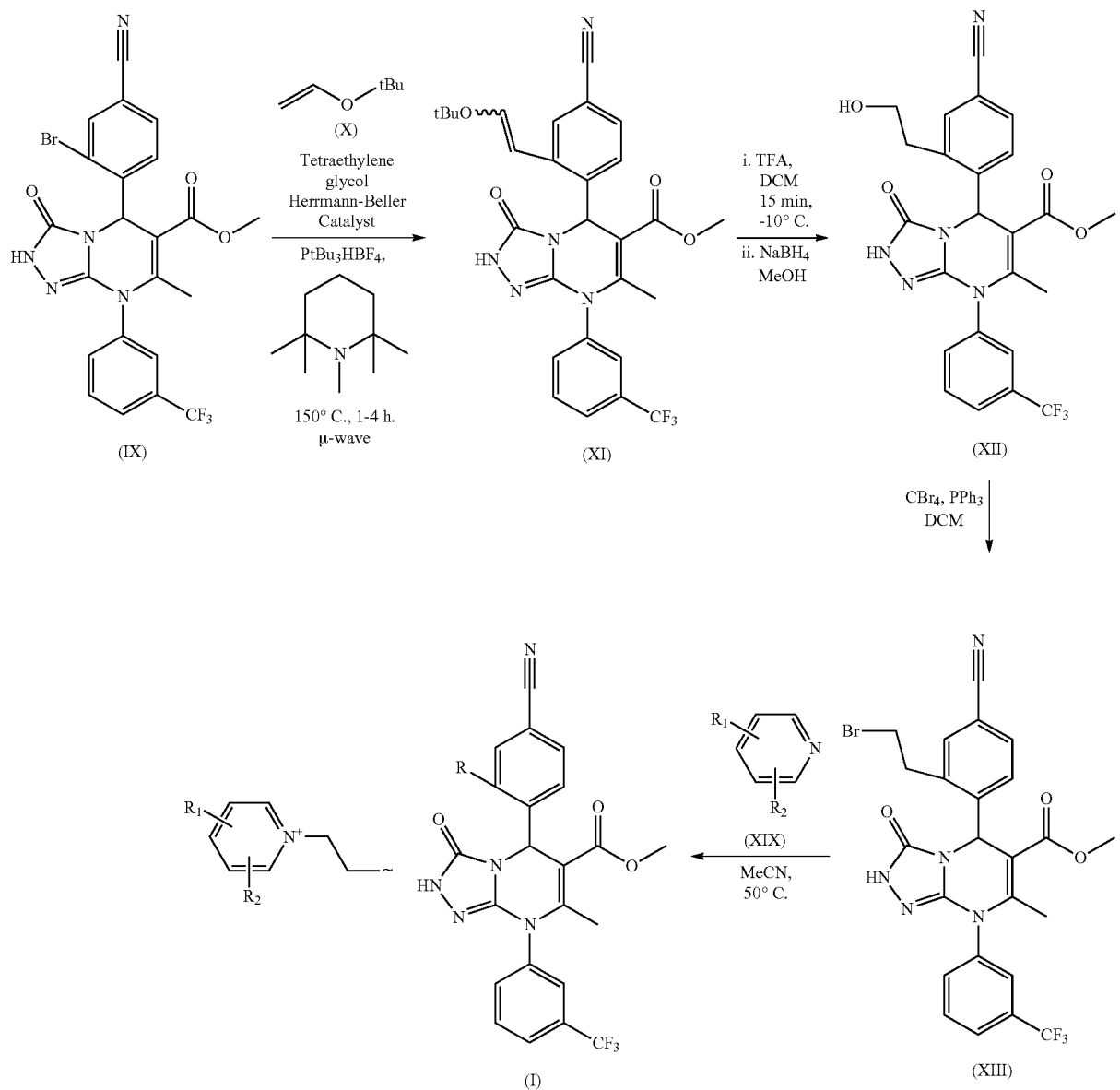

R = substituted pyridinium

General Experimental Details

Reactions were not carried out under an inert atmosphere unless specified and all solvents and commercial reagents were used as received.

Purification by chromatography refers to purification using the CombiFlash 0 Companion purification system or the Biotage SP1 purification system. Where products were purified using an Isolute® SPE Si II cartridge, 'Isolute SPE Si cartridge' refers to a pre-packed polypropylene column containing unbonded activated silica with irregular particles with average size of 50 μm and nominal 60 Å porosity. Fractions containing the required product (identified by TLC and/or LCMS analysis) were pooled, the organic fraction removed by evaporation, and the remaining aqueous fraction lyophilised, to give the final product. Where thin layer chromatography (TLC) has been used, it refers to silica gel TLC using plates, typically 3×6 cm silica gel on aluminium foil plates with a fluorescent indicator (254 nm), (e.g. Fluka 60778). Microwave experiments were carried out using a Biotage Initiator 60™ which uses a single-mode resonator and dynamic field tuning Temperature from 40-250° C. can be achieved, and pressures of up to 30 bar can be reached.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane.

Compound names were generated using the Autonom 2000 feature in MDL ISIS™/Draw 2.5 SP2 software.

Analytical LC-MS Conditions

LC-MS Method 1

The Waters ZQ quadrupole mass spectrometer with a C18-reverse-phase column (30×4.6 mm Phenomenex Luna 3 μm particle size), elution with A: water+0.1% formic acid; B: MeCN+0.1% formic acid. Gradient:

| Gradient - Time | flow (mL/min) | % A | % B |
|---|---|---|---|
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, ELS, UV (200 μl/min split to the ESI source with in-line HP1100 PDA detector)

MS ionisation method—Electrospray (positive and negative ion)

LC-MS Method 2

Waters Micromass ZMD quadrupole mass spectrometer with a C18-reverse-phase column (30×4.6 mm Phenomenex Luna 3 μm particle size), elution with A: water+0.1% formic acid; B: MeCN+0.1% formic acid. Gradient:

| Gradient - Time | flow(mL/min) | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (100 μl split to MS with in-line UV detector)

MS ionisation method—Electrospray (positive and negative ion)

LC-MS Method 3

Waters Micromass ZQ2000 mass spectrometer with a C18-reverse-phase column (100×2.1 mm Acquity BEH with 1.7 μm particle size) maintained at 40° C., elution with A: water+0.1% formic acid; B: MeCN+0.1% formic acid. Alternatively, where specified, a C18-reverse-phase (100× 2.1 mm Acquity UPLC BEH Shield 1.7 μm particle size) column was used.
Gradient:

| Gradient - Time | flow (mL/min) | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA

MS ionisation method—Electrospray (positive/negative ion).

LC-MS Method 4

Waters Platform LC quadrupole mass spectrometer with a C18-reverse-phase column (30×4.6 mm Phenomenex Luna 3 μm particle size), elution with A: water+0.1% formic acid; B: MeCN+0.1% formic acid. Gradient:

| Gradient - Time | flow (mL/min) | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (Split—200 μl/min split to the ESI source with in-line HP1100 DAD detection)

MS ionisation method—Electrospray (positive and negative ion).

LC-MS Method 5

Waters VG Platform II quadrupole spectrometer with a C18-reverse-phase column (30×4.6 mm Luna 3 μm particle size), elution with A: water+0.1% formic acid; B: MeCN+ 0.1% formic acid.
Gradient:

| Gradient - Time | flow | % A | % B |
|---|---|---|---|
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, ELS, UV (Split—200 μl/min split to the ESI source with in-line HP1050 DAD detection)

MS ionisation method—Electrospray (positive and negative ion)

MDAP System:

Instrumentation: Agilent 1260 infinity purifications system.
Agilent 6100 series single Quadrupole LC/MS
Column: XSELECT CSH Prep C18 5 μm OBD, 30×150 mm, RT
Mobile Phase A: 0.1% aqueous formic acid
Mobile Phase B: 0.1% formic acid in acetonitrile
Flow: 60 ml/min
Gradient Program: 10%-95%, 22 min, centred around a specific focused gradient Sample Injection of a 20-60 mg/ml solution in DMSO (+optional formic acid and water).

ABBREVIATIONS USED IN THE EXPERIMENTAL SECTION

DCM Dichloromethane
DMF N,N-dimethylformamide
DMSO Dimethylsulphoxide
$Et_2O$ Diethyl ether
EtOAc Ethyl acetate
HPLC High performance liquid chromatography
IMS Industrial methylated spirits
LC-MS Liquid chromatography-mass spectrometry
MeCN Acetonitrile
MDAP Mass Directed Automatic Purification
NBS N-Bromosuccinimide
Rt Retention time
RT Room temperature
THF Tetrahydro furan In the procedures that follow, some of the starting materials are identified through an "Intermediate" or "Example" number. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

Example 1

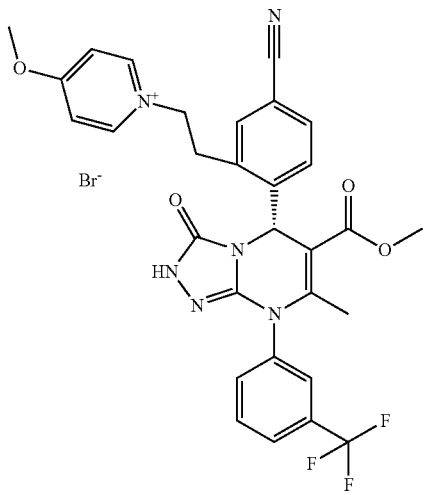

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-4-methoxy-pyridinium bromide Intermediate 1

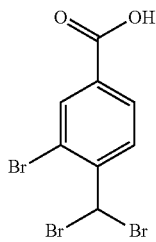

3-Bromo-4-dibromomethylbenzoic acid

3-Bromo-4-methylbenzoic acid (910 g, 4.23 mol, 1.0 eq.) and NBS (2010 g, 11.29 mol, 2.67 eq.) were dissolved in DCM (8.5 L) in a 20 L flange flask fitted with a mechanical stirrer. A slurry of AIBN (50 g, 0.3 mol, 0.07 eq.) in DCM (1 L) was then added, and the mixture irradiated under strong light (500 W) under a reflux condenser under an $N_2$ atmosphere. The internal temperature of the reaction rose from 17° C. to 41° C. and the initial white suspension became a pale orange suspension as it reached gentle reflux. After a total of 72 h. the reaction was complete and water (5 L) was added to the cloudy orange solution, which was stirred at RT for 1 h. The orange biphasic mixture was then left to stand overnight and was then concentrated in vacuo to give an orange distillate and a tan suspended solid. The solid was then collected by filtration, washed with water (2 L) and suction dried for 2 h to give the title compound as a tan coloured damp solid (1860 g).

LCMS (Method 1): Rt=3.39 min, m/z 369, 371, 373, 375 [M−H]

$^1$H NMR (300 MHz, DMSO): δ 8.14-8.03 (3H, m), 7.36 (1H, s).

Intermediate 2

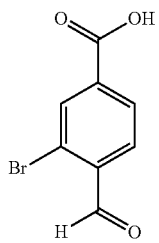

3-Bromo-4-formylbenzoic acid

Intermediate 1 (1860 g, 4.23 mol, 1.0 eq.) was suspended in water (5 L) and the slurry was heated to an internal temperature of 40° C. Solid $Na_2CO_3$ (1460 g, 13.77 mol, 3.25 eq.) was then added in small portions over a period of 20 min. Foaming resulted on initial addition, so EtOAc (0.2 L) was added to collapse the foam and suppress any further foaming. Once addition was complete, the brown suspension was heated to 90° C. over 40 min, then stirred at 90° C. for 90 min, then cooled to 40° C. over 90 min. EtOAc (1.5 L) was added, followed by addition of aqueous concentrated HCl via dropping funnel (0.7 L), resulting in vigorous evolution of $CO_2$ gas and evaporation of most of the EtOAc. Further EtOAc (1 L) was added to wash the foaming product from the condenser and the walls of the reactor, then additional EtOAc (0.3 L) was added and the thick slurry was stirred at RT overnight. The slurry was then heated to 40° C. and further aqueous concentrated HCl was added via dropping funnel with vigorous stirring over 45 min, resulting in $CO_2$ gas evolution, evaporation of most of the EtOAc and formation of a solid. Stirring was ceased, and the solid floated to the top of the aqueous mixture (pH 1). The majority of the aqueous layer was separated (ca. 5 L) and then 2-MeTHF (5 L) was added. The clear aqueous layer was then removed, and the organic layer diluted to 10 L with additional 2-MeTHF, and warmed to 50° C. to give a dark orange solution. The organic layer was then washed with 1 M HCl (0.5 L), evaporated, and azeotroped with toluene to afford the title compound as a tan coloured solid (960.3 g).

LCMS (Method 4): Rt 2.73 min, m/z 227 [M($^{79}$Br)+H]$^+$ $^1$H NMR (300 MHz, DMSO): δ 10.26 (1H, d, J=0.8 Hz), 8.20 (1H, d, J=1.5 Hz), 8.08-8.04 (1H, m), 7.95 (1H, d, J=8.0 Hz).

Intermediate 3

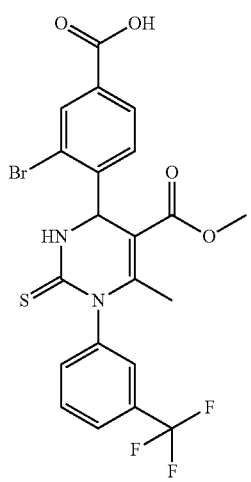 [SMILES: COC(=O)C1=C(C)N(c2cccc(C(F)(F)F)c2)C(=S)N[C@@H]1c1ccc(C(=O)O)cc1Br]

4-(2-Bromo-4-carboxyphenyl)-6-methyl-2-thioxo-1-(3-trifluoromethylphenyl)-1,2,3,4-tetrahydropyrimidine-5-carboxylic acid methyl ester Intermediate 2 (458 g, 2 mol, 1.0 eq.), methyl acetoacetate (274.4 g, 255 mL, 2.36 mol, 1.18 eq.) and 3-trifluoromethylphenyl thiourea (519 g, 2.36 mol, 1.18 eq.), were charged to a 10 L jacketed reactor under a $N_2$ atmosphere, and suspended in THF (4.6 L) and while stirring, was cooled to −10° C. (internal temperature −3° C.). Polyphosphoric acid (1650 g, 3.6 wt eq.), was prewarmed in a water bath at 50° C., then added in one portion, resulting in an immediate exotherm, and the internal temperature rose to 19° C. The resulting orange mixture was then warmed to 75° C. in 10° C. increments to a gentle reflux, and the reaction stirred at this temperature for 20 h. The reaction was then cooled to 20° C. and the bulk of THF removed in vacuo to give a dark orange viscous oil, which was then diluted with water (5 L) and $Et_2O$ (5 L). The aqueous layer was separated and extracted again with $Et_2O$ (2×2 L) and the combined organics were subsequently washed with water (1 L), brine (1 L) and dried ($Na_2SO_4$) and filtered through Celite to remove any fine particulates. The filtered solution was then concentrated in vacuo to give a viscous orange gum which was resuspended in $Et_2O$ (ca. 1.5 L) and left to stand overnight. The resulting suspension was filtered and the solid collected was rinsed with $Et_2O$ (0.5 L) and dried in a vacuum oven at 50° C. (8 mbar) for 4 days to afford the title compound (754 g).

LCMS (Method 1): Rt 3.52 min, m/z 529 [M($^{79}$Br)+H]$^+$ $^1$H NMR (300 MHz, DMSO): δ 10.15 (1H, d, J=3.5 Hz), 8.11 (1H, d, J=1.6 Hz), 8.05 (1H, dd, J=8.1, 1.7 Hz), 7.92-7.64 (5H, m), 5.80 (1H, d, J=2.9 Hz), 3.53 (3H, s), 2.07 (3H, s).

Intermediate 4

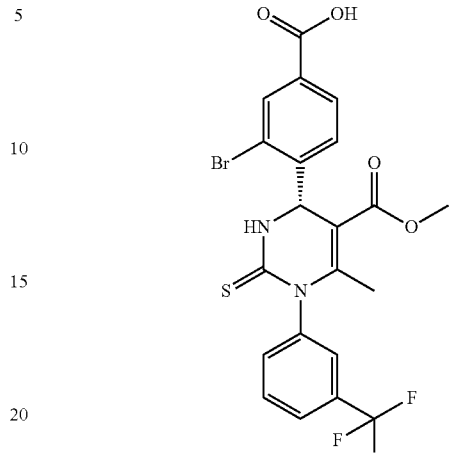

(S)-4-(2-Bromo-4-carboxy-phenyl)-6-methyl-2-thioxo-1-(3-trifluoromethyl-phenyl)-1,2,3,4-tetrahydro-pyrimidine-5-carboxylic acid methyl ester Intermediate 3 (151.7 g, 0.29 mol, 1.0 eq.) was dissolved in dioxane (2 L) and heated to 80° C. The resulting suspension was filtered to remove any inorganic residues and the clear solution was again heated to 80° C. and (+)-Cinchonine (88 g, 0.29 mol, 1.0 eq) was added, resulting in a clear solution. The resultant mixture was allowed to cool slowly and crystallise. After 3 h, the resulting solid was filtered and washed with cold dioxane. The solid was resuspended in hot dioxane (85° C.) and allowed to cool and crystallise overnight. The resulting crystals were filtered off, washed with cold dioxane, and the solid recrystallised again from hot dioxane. The final recrystallization solids were filtered off and air-dried to give the intermediate (+)-Cinchonine salt as a white solid 83.2 g (68%).

The optical purity of the resolved (+)-Cinchonine salt was determined by partitioning between 1 M HCl and EtOAc; the organic layer was separated, concentrated in vacuo and then redissolved in 20% IPA/n-heptane with 0.1% TFA and subjected to chiral analytical HPLC (ChiralPak IA, 5 µM 4.6×250 mm), eluting with 20% IPA/n-heptane (+0.1% TFA) at 1 mL/min and a wavelength of 254 nm. The racemic product was also checked by chiral HPLC; Retention times of 14.8 and 42.5 mins were observed for a racemic sample and the desired enantiomer was eluted at 42.5 mins and was found to be greater than 99.5ee %.

The intermediate (+)-Cinchonine salt (83.2 g, 101.75 mmol) was liberated by partitioning between EtOAc (1 L) and 1 M HCl (1 L). The aqueous layer was extracted again with EtOAc (2×0.5 L) and the combined organic layers washed with 1 M HCl (0.5 L), then brine (0.25 L), dried ($Na_2SO_4$) and concentrated in vacuo to give the title compound as a white solid (45.45 g).

Intermediate 5

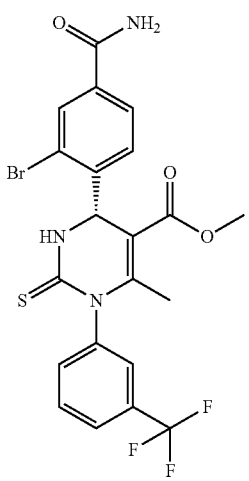 [SMILES: COC(=O)C1=C(C)N(c2cccc(C(F)(F)F)c2)C(=S)N[C@@H]1c1ccc(C(N)=O)cc1Br]

(S)-4-(2-Bromo-4-carbamoyl-phenyl)-6-methyl-2-thioxo-1-(3-trifluoromethyl-phenyl)-1,2,3,4-tetrahydro-pyrimidine-5-carboxylic acid methyl ester Intermediate 4 (93.8 g, 0.18 mol) was dissolved in THF (1 L) and 1,1'-carbonyldiimidazole (57.5 g, 0.35 mol, 2.0 eq.) was added portion-wise and left to stir at RT until gas evolution had ceased. Aqueous ammonia solution (33%, 330 mL) was then added drop-wise, ensuring the internal temperature did not exceed 10° C. (exotherm observed on initial addition). The reaction was left to stir at RT for 2 h, then brine was added and the layers were separated. The organic phase was washed with aqueous 1 M HCl (2×) and the acidic layer further extracted with EtOAc. The combined organic layers were washed with brine, dried (Na$_2$SO$_4$), filtered and concentrated in vacuo to afford the title compound as a colourless foam (87.3 g).

LCMS (Method 2): Rt 3.44 min, m/z 528 [M($^{79}$Br)+H]$^+$ $^1$H NMR (300 MHz, DMSO): δ 10.12 (1H, d, J=2.6 Hz), 8.12 (1H, s), 8.11 (1H, d, J=1.7 Hz), 7.96 (1H, dd, J=8.1, 1.7 Hz), 7.88-7.77 (2H, m), 7.75-7.63 (3H, m), 7.54 (1H, s), 5.78 (1H, s), 3.54 (3H, s), 2.07 (3H, s).

Intermediate 6

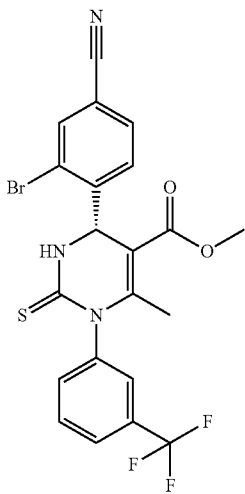 [SMILES: COC(=O)C1=C(C)N(c2cccc(C(F)(F)F)c2)C(=S)N[C@@H]1c1ccc(C#N)cc1Br]

(S)-4-(2-Bromo-4-cyanophenyl)-6-methyl-2-thioxo-1-(3-trifluoromethylphenyl)-1,2,3,4-tetrahydropyrimidine-5-carboxylic acid methyl ester Intermediate 5 (87.3 g, 0.165 mol) was dissolved in DMF (400 mL) and cooled to 0-5° C. in an ice bath. Phosphorous oxychloride (62.0 g, 37.0 mL, 2.5 eq.) was then added drop-wise, ensuring the internal temperature did not exceed 10° C. Once addition was complete, the yellow solution was stirred at 0-5° C. for 15 min, then poured into a mixture of solid 2 M Na$_2$CO$_3$ and ice. A yellow precipitate formed and the slurry was aged for 1 h, then the solid was filtered, washed with water and dried in a vacuum oven over P$_2$O$_5$ at 40-45° C. NMR analysis of the resultant product still showed starting material remaining so the reaction was repeated again using a further 20 mL phosphorous oxychloride. NMR of the resulting solid showed the product to be an adduct with POCl$_3$. Therefore, the solid was dissolved in absolute EtOH (1000 mL) and the suspension warmed to aid dissolution. Saturated aqueous NaHCO$_3$ solution (250 mL) was then added and the mixture was heated to 40° C. and stirred for 2 h. The resultant mixture was then poured into water (500 mL) and the resulting white solid filtered off, washed with water and air dried to afford the title compound (77.5 g).

LCMS (Method 2): Rt 3.94 min, m/z 510 [M($^{79}$Br)+H]$^+$ $^1$H NMR (300 MHz, DMSO): δ 10.18 (1H, d, J=2.7 Hz), 8.24 (1H, d, J=1.5 Hz), 7.96 (1H, dd, J=8.0, 1.6 Hz), 7.89-7.76 (3H, m), 7.74-7.64 (2H, m), 5.8 (1H, s), 3.53 (3H, s), 2.06 (3H, s).

Intermediate 7

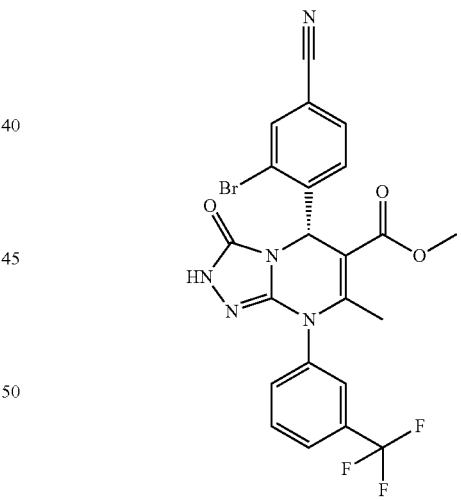

(S)-5-(2-Bromo-4-cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester Intermediate 6 (30.3 g, 59.4 mmol) was dissolved in DCM (500 mL), 2,6-lutidine (19.7 mL, 169 mmol) was added and the solution was cooled to 2° C. While stirring, triphosgene (5.58 g, 18.8 mmol) was then added over a period of 3 min. After 5 min, the reaction was warmed to RT and stirred for 25 min. The reaction was cooled to 2-3° C. and the solution was then transferred via cannula to a cooled (7° C.) mixture of hydrazine solution (1 M in THF, 170 mL) in MeCN (150 mL). The mixture was stirred at 7° C. for a further 5 min. After 2.25 h, the reaction mixture was washed with water, 10% citric acid solution (to remove residual lutidine), water and 50% saturated brine and the organic phase was dried (Na$_2$SO$_4$), filtered and concentrated in vacuo. Further purification was undertaken by chromatography using silica-gel, and eluting with 40% to 100% EtOAc in cyclohexane to afford Int 7 as a cream coloured solid (17.8 g)

LCMS (Method 3): Rt 3.61 min, m/z 534 [M($^{79}$Br)+H]$^+$ $^1$H NMR (300 MHz, CDCl$_3$): δ 8.36 (1H, s), 7.88 (1H, d, J=1.5 Hz), 7.83-7.79 (1H, m), 7.73 (1H, t, J=8.0 Hz), 7.65-7.60 (2H, m), 7.59-7.50 (2H, m), 6.39 (1H, d, J=1.0 Hz), 3.62 (3H, s), 2.25 (3H, d, J=1.0 Hz).

The chiral purity was analysed by Chiralpak IC chiral HPLC column (5 μm particle size, 5% MeOH/DCM, flow rate 5 mL/min) and gave Rt=5.83 min. (100% ee). A racemic sample (Intermediate 4) gave Rt for first and second eluting enantiomers of 3.58 and 5.85 min, respectively.

Intermediate 8

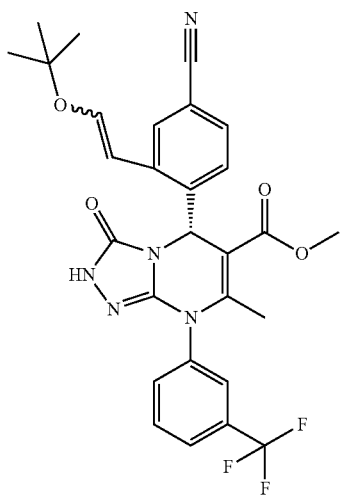 [SMILES: COC(=O)C1=C(C)N(c2cccc(C(F)(F)F)c2)c2n[nH]c(=O)n2[C@@H]1c1ccc(C#N)cc1C=COC(C)(C)C]

(R)-5-[2-(2-tert-Butoxy-vinyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester An autoclave was charged with a mixture of Intermediate 7 (10 g, 18.72 mmol), 2-methyl-2-vinyloxy-propane (6.55 g, 65.50 mmol), tri-tertiary-butyl phosphonium tetrafluoroborate (540 mg, 1.86 mmol), Herrmann-Beller catalyst (trans-di(g-acetato)bis(0-di-o-tolyl-phosphino)benzyl)dipalladium (II)) (880 mg, 0.94 mmol), 1,2,2,6,6-pentamethylpiperidine (11.5 g, 74.20 mmol). Tetra-ethylene glycol (140 mL) was added and the resulting solution degassed under Argon. The mixture was then heated at 150° C. for 1 h. The mixture was cooled, diluted with EtOAc and aqueous 10% citric acid and the organic extract was washed with water and brine, then dried (Na$_2$SO$_4$) and concentrated in vacuo. The resultant residue was purified by chromatography, eluting with 25-75% EtOAc in cyclohexane to give the title compound as a [3:1] mixture of E/Z isomers and as a yellow foam (7.95 g).

LC-MS (Method 5): Rt=3.87 min, m/z=554.2 [M+H]$^+$1

Intermediate 9

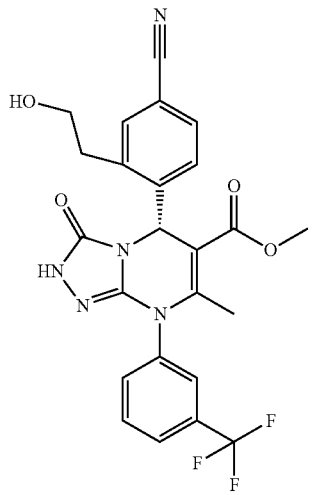 [SMILES: COC(=O)C1=C(C)N(c2cccc(C(F)(F)F)c2)c2n[nH]c(=O)n2[C@@H]1c1ccc(C#N)cc1CCO]

(R)-5-[4-Cyano-2-(2-hydroxy-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester A solution of Intermediate 8 (7.87 g, 14.20 mmol) in DCM (130 mL) was cooled to −10° C. using a salt/ice bath and treated drop-wise with TFA (6.35 mL, 85.47 mmol). After stirring the solution at −10° C. for 2 h the resulting solution was poured into ice-cold aqueous Na$_2$CO$_3$ solution. The organic phase was separated and the aqueous phase was further extracted with DCM (70 mL) and the combined DCM extract returned to the salt/ice bath at −5° C. Sodium borohydride (1.57 g, 41.42 mmol) was added portion-wise and after stirring for 15 minutes, MeOH (32 mL) was added to the resulting mixture. The reaction was stirred at −5° C. for 1.5 h, water was added and the resulting mixture allowed to stir vigorously for 15 mins prior to separation of the organic phase. The aqueous phase was further extracted with DCM and the combined organic extract was washed with brine, dried (Na$_2$SO$_4$) and concentrated in vacuo. The resultant residue was purified by chromatography, eluting with EtOAc and gave the title compound as a cream solid (3.7 g).

LC-MS (Method 5): Rt=3.17 min, m/z=500.1 [M+H]$^+$

Intermediate 10

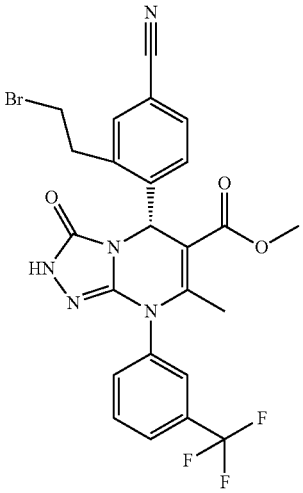 [SMILES: COC(=O)C1=C(C)N(c2cccc(C(F)(F)F)c2)c2n[nH]c(=O)n2[C@@H]1c1ccc(C#N)cc1CCBr]

(R)-5-[2-(2-Bromo-ethyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester Intermediate 9 (23 g, 46.1 mmol) was stirred in DCM (400 mL) at RT as tetrabromomethane (22.95 g, 69.1 mmol) was added. Triphenylphosphine (18.11 g, 69.1 mmol) was then added in portions over 10 min. The reaction mixture was briefly cooled in ice in order to maintain RT (a small initial exotherm occurs). Stirring was continued at RT for 3 h. The mixture was washed with water, the organic phase dried ($Na_2SO_4$), filtered and evaporated and the residue chromatographed, eluting with a gradient of 40% to 75% EtOAc in cyclohexane, yielding the title compound as a white solid (23.6 g).

LC-MS (Method 5): Rt=3.83 min, m/z=562.1 [M($^{79}$Br)+H]$^-$

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-4-methoxy-pyridinium bromide (Example 1)

A mixture of Intermediate 10 (30 mg, 53 μmmol) and 4-methoxy pyridine (17.5 mg, 160 μmol) in MeCN (1 mL) was warmed to 50° C. in a sealed tube for 18 h then concentrated in vacuo. The crude product was partitioned between water and EtOAc and the aqueous layer separated and freeze dried to give the title compound as a white electrostatic solid (15 mg).

LC-MS (Method 3): Rt=3.78 min, m/z=591.1 [M]$^+$

The following examples were prepared from Intermediate 10 and the appropriately substituted pyridine compounds using an analogous method to that used for Example 134:

| Ex | Structure | Name | LC-MS (Method 3) |
|---|---|---|---|
| 2 | 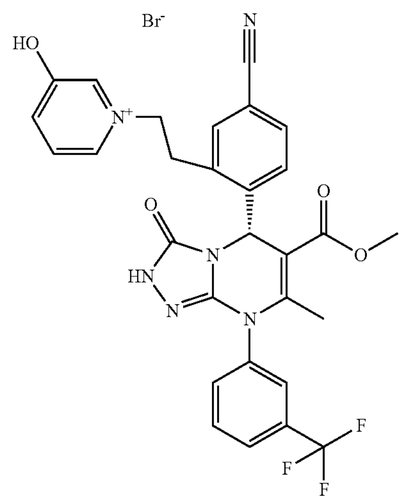 [SMILES: COC(=O)C1=C(C)N(c2cccc(C(F)(F)F)c2)c2n[nH]c(=O)n2[C@@H]1c1ccc(C#N)cc1CC[n+]1cccc(O)c1 ; [Br-]] | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-hydroxy-pyridinium bromide | Rt = 3.60 min, m/z = 577.1 [M]$^+$ |
| 3 | 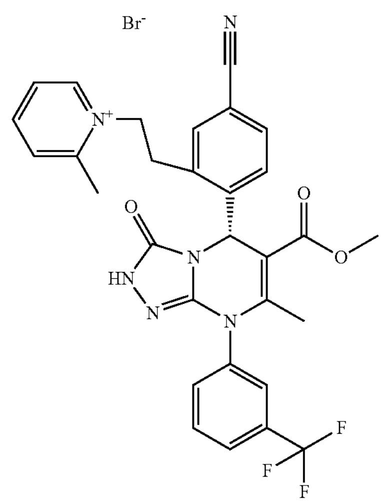 [SMILES: COC(=O)C1=C(C)N(c2cccc(C(F)(F)F)c2)c2n[nH]c(=O)n2[C@@H]1c1ccc(C#N)cc1CC[n+]1ccccc1C ; [Br-]] | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2-methyl-pyridinium bromide | Rt = 3.65 min, m/z = 575.1 [M]$^+$ |

-continued

| Ex | Structure | Name | LC-MS (Method 3) |
|---|---|---|---|
| 4 | 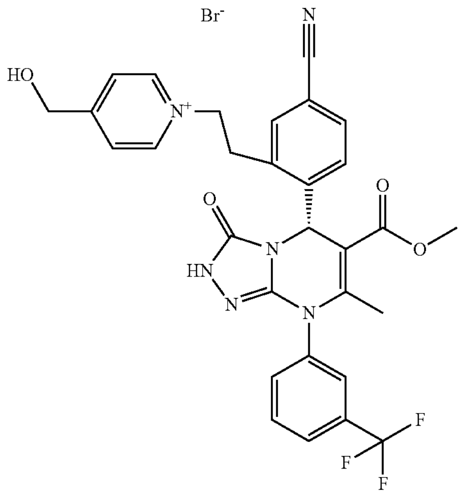 [SMILES: COC(=O)C1=C(C)N(c2cccc(C(F)(F)F)c2)c2n[nH]c(=O)n2[C@@H]1c1ccc(C#N)cc1CC[n+]1ccc(CO)cc1 ; [Br-]] | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-4-hydroxymethyl-pyridinium bromide | Rt = 3.51 min, m/z = 591.1 [M]+ |
| 5 | 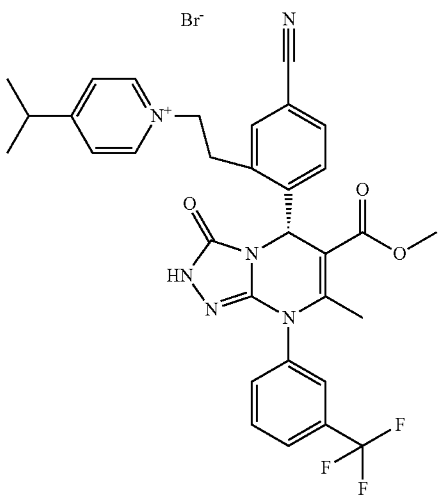 [SMILES: COC(=O)C1=C(C)N(c2cccc(C(F)(F)F)c2)c2n[nH]c(=O)n2[C@@H]1c1ccc(C#N)cc1CC[n+]1ccc(C(C)C)cc1 ; [Br-]] | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-4-isopropyl-pyridinium bromide | Rt = 3.82 min, m/z = 603.2 [M]+ |
| 6 | 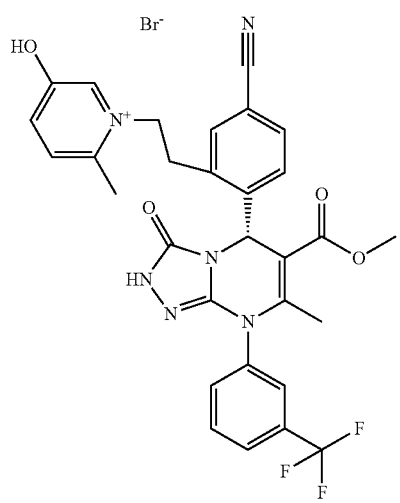 [SMILES: COC(=O)C1=C(C)N(c2cccc(C(F)(F)F)c2)c2n[nH]c(=O)n2[C@@H]1c1ccc(C#N)cc1CC[n+]1cc(O)ccc1C ; [Br-]] | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-5-hydroxy-2-methyl-pyridinium bromide | Rt = 3.64 min, m/z = 591.1 [M]+ |

| Ex | Structure | Name | LC-MS (Method 3) |
|---|---|---|---|
| 7 | 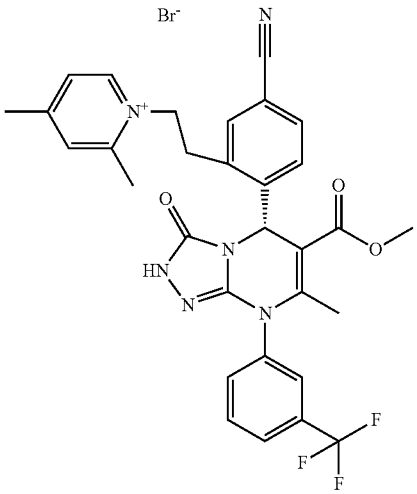 | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2,4-dimethyl-pyridinium bromide | Rt = 3.69 min, m/z = 589.1 [M]+ |
| 8 | 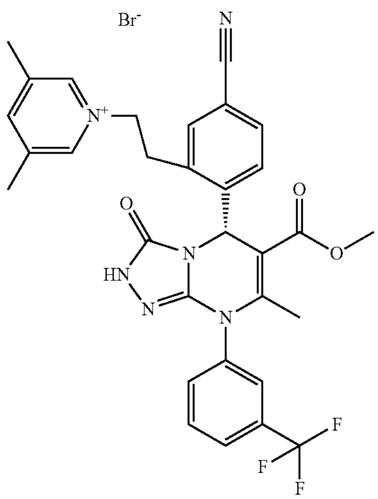 [SMILES: COC(=O)C1=C(C)N(c2cccc(C(F)(F)F)c2)c2n[nH]c(=O)n2[C@@H]1c1ccc(C#N)cc1CC[n+]1cc(C)cc(C)c1 ; [Br-]] | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3,5-dimethyl-pyridinium bromide | Rt = 3.71 min, m/z = 589.2 [M]+ |
| 9 | 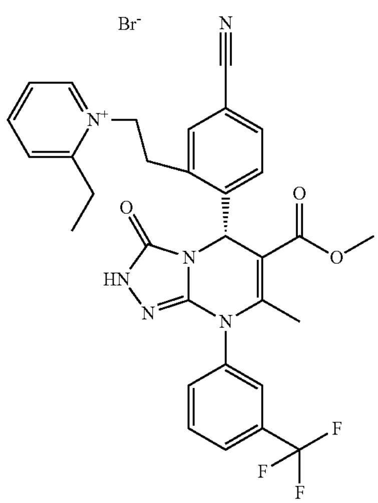 [SMILES: CCc1cccc[n+]1CCc1cc(C#N)ccc1[C@@H]1C(C(=O)OC)=C(C)N(c2cccc(C(F)(F)F)c2)c2n[nH]c(=O)n21 ; [Br-]] | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2-ethyl-pyridinium bromide | Rt = 3.74 min, m/z = 589.1 [M]+ |

-continued

| Ex | Structure | Name | LC-MS (Method 3) |
|---|---|---|---|
| 10 | (structure) | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2-(2-hydroxy-ethyl)-pyridinium bromide | Rt = 3.55 min, m/z = 605.1 [M]$^+$ |
| 11 | (structure) | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-4-ethyl-pyridinium bromide | Rt = 3.72 min, m/z = 589.1 [M]$^+$ |

Biological Assay

Compounds of this invention were tested for potency in a human neutrophil elastase (HNE) enzyme activity assay.

FINE Enzyme Assay

Assays were performed in 96-well plates in a total assay volume of 100 μL. The final concentration of elastase enzyme (human leukocyte elastase, Sigma E8140) was 0.00072 U/mL. The peptide substrate (MeOSuc-Ala-Ala-Pro-Val-AMC, Calbiochem #324740) was used at a final concentration of 100 μM. The final concentration of DMSO was 1% in the assay buffer (0.05M Tris.HCl, 0.1M NaCl, 0.1M $CaCl_2$, 0.0005% brij-35, pH 7.5). The enzymatic reaction was started by addition of the enzyme and incubated at 25° C. for 30 minutes. After incubation, the reaction was stopped by addition of soybean trypsin inhibitor (Sigma T9003) at a final concentration of 50 μg/well. Fluorescence was measured using a Molecular Devices fluorescence plate reader using 380 nm excitation and 460 nm emission wavelengths.

A dose response to each compound was performed and the effect of compound in each experiment was expressed as a percentage inhibition of the control enzyme fluorescence. Dose response curves were plotted and compound potency ($IC_{50}$) was determined. Compounds were tested in at least two separate experiments.

$IC_{50}$s for tested Examples, representative of the invention, are shown in the following table:

| Example | HNE inhibition |
|---|---|
| 1-11 | ++++ |

In the table above, HNE enzyme inhibition ($IC_{50}$ values) are indicated as follows: >500 nM '+'; 100-500 nM '++'; 20-100 nM '+++'; <20 nM '++++'.

The invention claimed is:
1. A compound selected from the group consisting of:
1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3a]pyrimidin-5-yl]-phenyl}-ethyl)-4-methoxy-pyridinium bromide;
1-(2-{5-Cyano-2-[(R)-6-methoxycarbonyl-7-methyl-3-oxo-8-(3-trifluoromethyl-phenyl)-2,3,5,8-tetrahydro-

[1,2,4]triazolo[4,3-a]pyrimidin-5-yl]-phenyl}-ethyl)-3-hydroxy-pyridinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2-methyl-pyridinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-4-hydroxymethyl-pyridinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-4-isopropyl-pyridinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-5-hydroxy-2-methyl-pyridinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2,4-dimethyl-pyridinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3,5-dimethyl-pyridinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2-ethyl-pyridinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-2-(2-hydroxy-ethyl)-pyridinium bromide; and 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-4-ethyl-pyridinium bromide;

or a pharmaceutically acceptable salt of said compound.

2. A compound of formula (I)" or a pharmaceutically acceptable salt thereof:

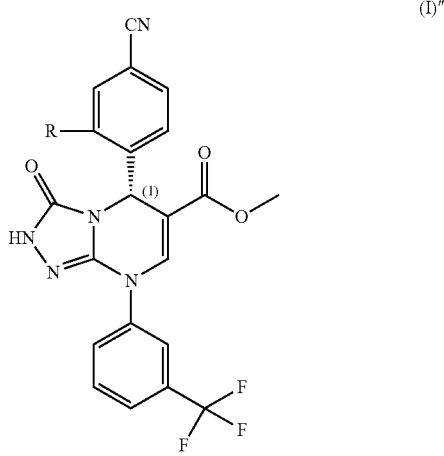

(I)"

wherein the group R is selected from the group consisting of 4-methoxy-pyridinyl;

3-hydroxy-pyridinyl;

2-methyl-pyridinyl;

4-hydroxymethyl-pyridinyl;

4-isopropyl-pyridinyl;

5-hydroxy-2-methyl-pyridinyl;

2,4-dimethyl-pyridinyl;

3,5-dimethyl-pyridinyl;

2-ethyl-pyridinyl;

2-(2-hydroxy-ethyl)-pyridinyl; and 4-ethyl-pyridinyl.

3. A pharmaceutical composition, comprising a compound or salt according to claim 1 and a pharmaceutically acceptable carrier or excipient.

4. A pharmaceutical composition of claim 3, which is adapted for oral administration or administration by a pulmonary route.

5. A method of treating a disease or condition, comprising administering to a subject in need thereof an effective amount of a compound or salt according to claim 1, wherein said disease or condition is chronic obstructive pulmonary disease, chronic bronchitis, lung fibrosis, pneumonia, acute respiratory distress syndrome, pulmonary emphysema, smoking-induced emphysema or asthma.

6. A method according to claim 5, wherein said disease or condition is chronic obstructive pulmonary disease.

7. A method according to claim 5, wherein said disease or condition is chronic bronchitis.

8. A method according to claim 5, wherein said disease or condition is lung fibrosis.

9. A method according to claim 5, wherein said disease or condition is pneumonia.

10. A method according to claim 5, wherein said disease or condition is acute respiratory distress syndrome.

11. A method according to claim 5, wherein said disease or condition is pulmonary emphysema.

12. A method according to claim 5, wherein said disease or condition is smoking-induced emphysema.

13. A method according to claim 5, wherein said disease or condition is asthma.

* * * * *